US006295671B1

United States Patent
Reesby et al.

(10) Patent No.: US 6,295,671 B1
(45) Date of Patent: Oct. 2, 2001

(54) MEDICAL SURGICAL TABLE INCLUDING INTERCHANGEABLE ORTHOPEDIC ATTACHMENT AND SCANNING TABLE

(75) Inventors: Cyril F. Reesby; James A. Schaefer, both of Troy, OH (US)

(73) Assignee: Ohio Medical Instrument Company, Inc., Cincinnati, OH (US)

(*) Notice: Subject to any disclaimer, the term of this patent is extended or adjusted under 35 U.S.C. 154(b) by 0 days.

(21) Appl. No.: 09/263,403

(22) Filed: Mar. 5, 1999

Related U.S. Application Data

(60) Provisional application No. 60/077,131, filed on Mar. 6, 1998.

(51) Int. Cl.[7] ..................................................... A61G 13/00
(52) U.S. Cl. ....................................... 5/600; 5/620; 5/621
(58) Field of Search ................................. 5/600, 601, 621, 5/622, 623, 624, 507.1; 606/241, 240, 245; 602/32; 108/11, 13, 57.1, 57.17, 62, 143, 137

(56) References Cited

U.S. PATENT DOCUMENTS

| | | | |
|---|---|---|---|
| D. 243,285 | * | 2/1977 | Langren .............................. 5/621 X |
| 2,872,259 | | 2/1959 | Thorpe . |
| 3,065,344 | | 11/1962 | Chervenka . |
| 3,745,996 | * | 7/1973 | Rush .................................. 128/84 B |
| 3,947,686 | | 3/1976 | Cooper et al. . |
| 4,054,282 | * | 10/1977 | Hammer .............................. 5/623 X |
| 4,148,472 | | 4/1979 | Rais et al. . |
| 4,501,414 | | 2/1985 | Mason et al. . |
| 4,552,346 | | 11/1985 | Schnelle et al. . |
| 4,635,914 | * | 1/1987 | Kabanek .............................. 269/328 |
| 4,872,656 | | 10/1989 | Bredngorg et al. . |
| 4,989,848 | | 2/1991 | Monroe . |
| 5,199,060 | | 3/1993 | Kato . |
| 5,287,575 | * | 2/1994 | Allen et al. ............................... 5/623 |

FOREIGN PATENT DOCUMENTS 0396866   3/1990   (EP) .

OTHER PUBLICATIONS

Chick CLT : Chick–Langren Orthopedic & Surgical Operating Table, 1995.
AMSCO OrthoVision Orthopedic Table, 1992.
Schaerer, AXIS.
Chick–Langren Orthopedic & Surgical Operating Table Technique Manual.
Stille, Image Guided Surgical Tables, B–140–102–GB9711, 1997.
Chick by Midmark Imagable Orthopaedic Table, 1997.
Stille, Image Guided Surgical Tables, B–140–101–GB9711, 1997.

* cited by examiner

*Primary Examiner*—Lynne H. Browne
*Assistant Examiner*—Fredrick Conley
(74) *Attorney, Agent, or Firm*—Wood, Herron & Evans, L.L.P.

(57) ABSTRACT

An articulated surgical table configured to alternatively receive an orthopedic attachment and a scanning table attachment. The orthopedic attachment is provided with a frame having a plurality of mounting points for mounting two detachable spar members. Either or both of the spar members may be mounted to the frame to provide the desired level of patient support and operator access. In addition, a pelvic support plate is supported on top of the frame and is formed with an asymmetrical construction. The pelvic support plate includes a cutout area on a front corner thereof for permitting additional access to the affected or broken leg of a patient. The plate may be flipped over to position the cutout area on the opposite side of the patient, depending on the location of the affected leg. The scanning table attachment includes an X-ray transparent table structure formed with a length sufficient to support a patient from the perineum to the top of the patient's head, and permits X-ray imaging from all angles around the table without obstruction.

26 Claims, 9 Drawing Sheets

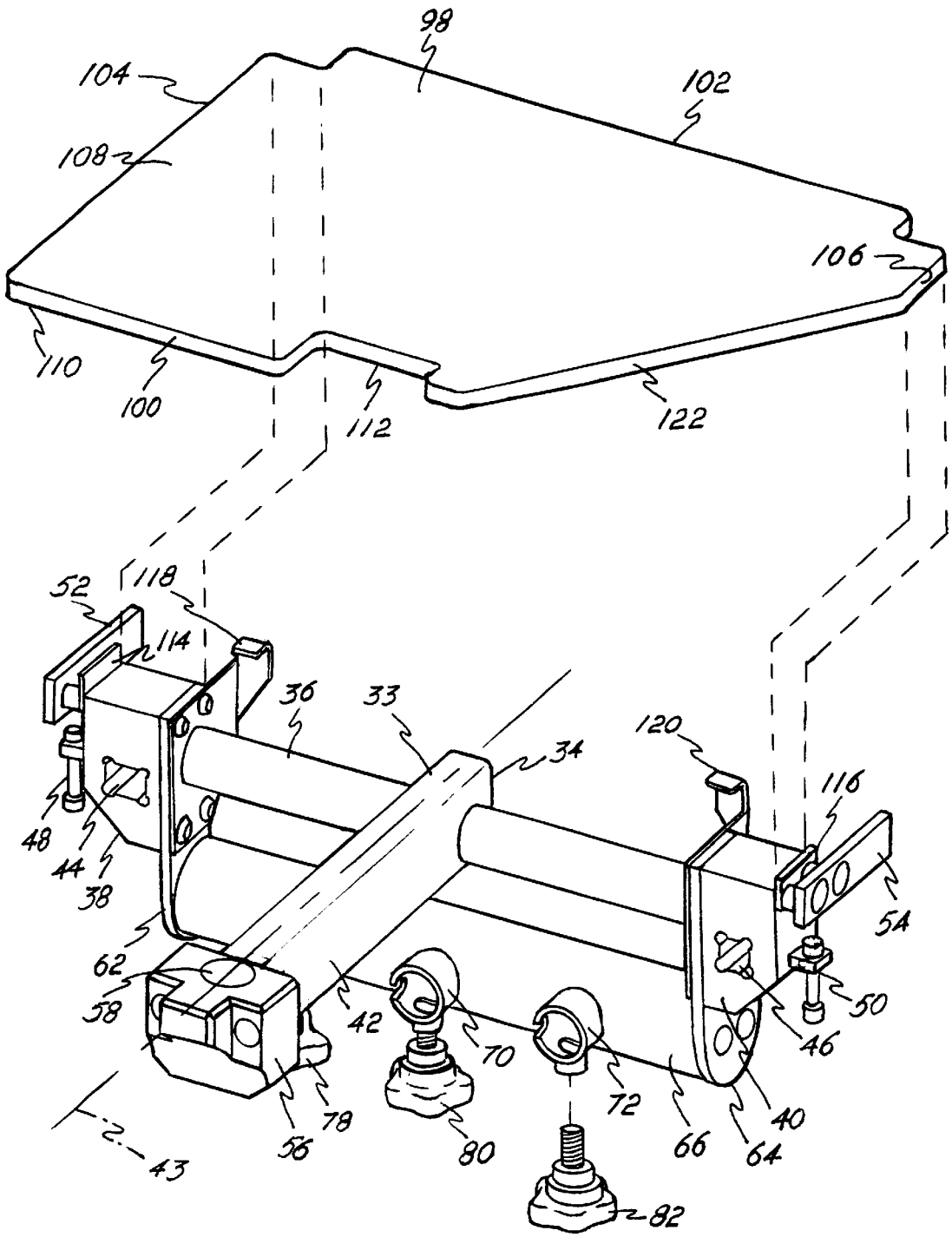

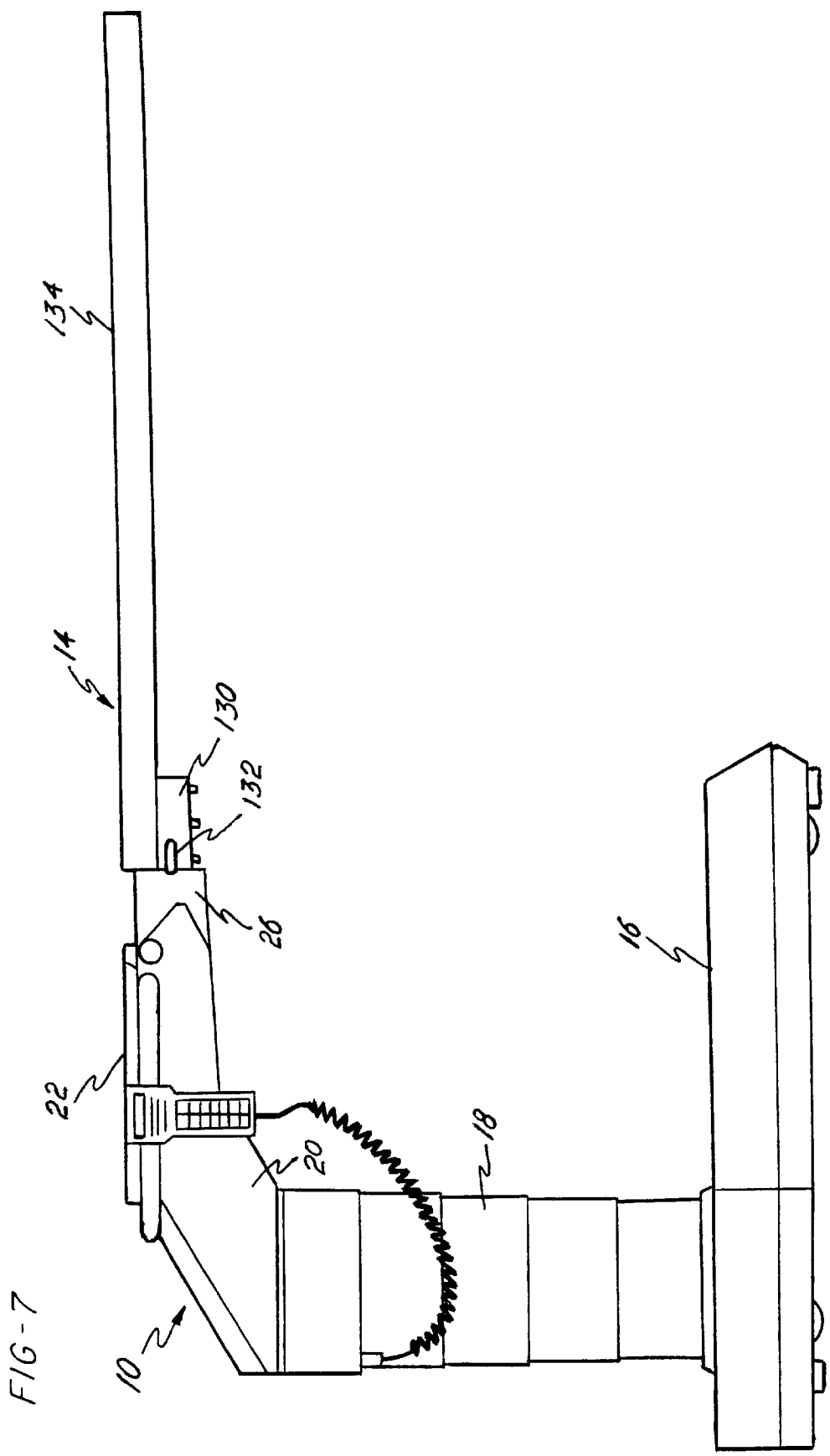

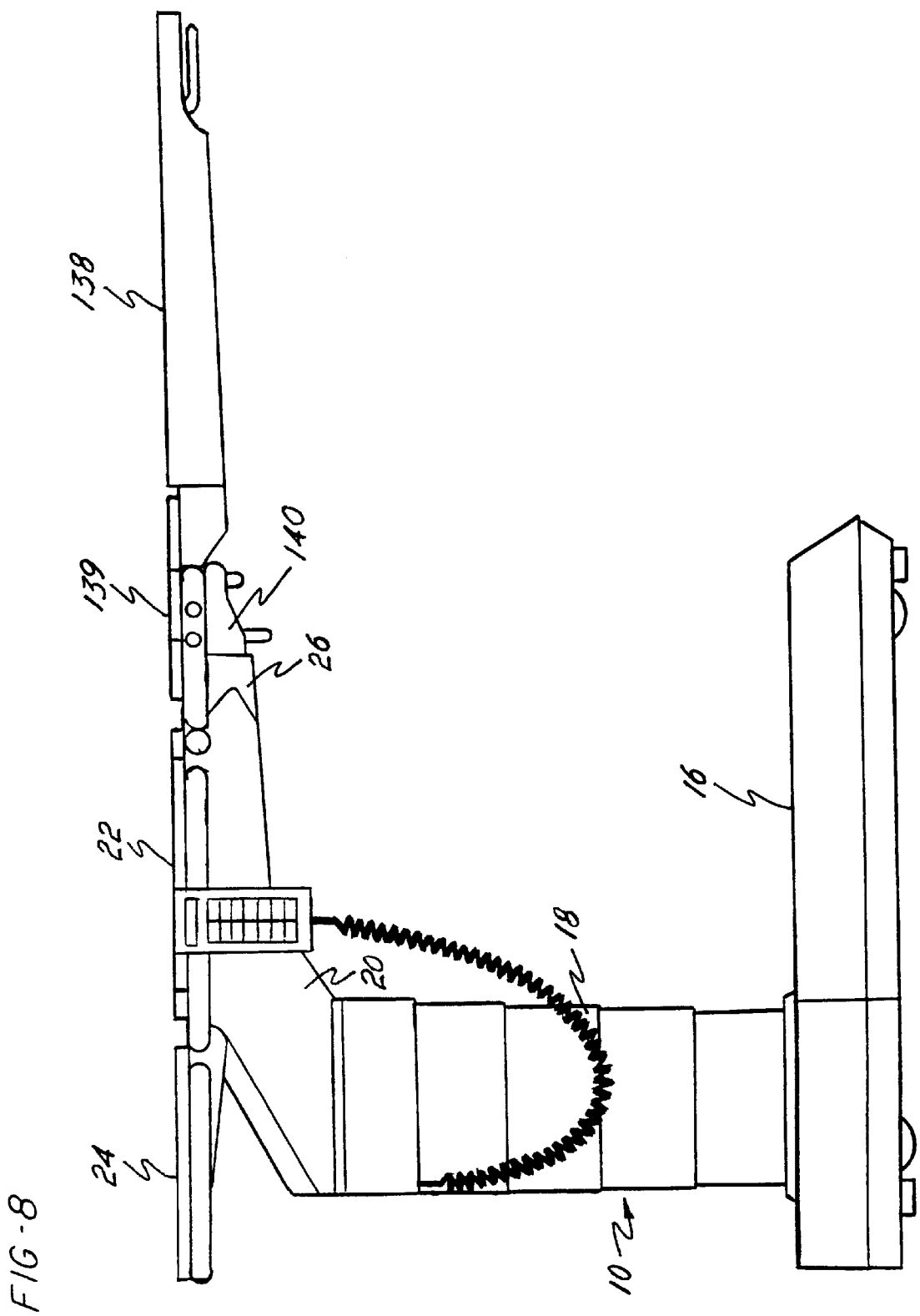

MEDICAL SURGICAL TABLE INCLUDING INTERCHANGEABLE ORTHOPEDIC ATTACHMENT AND SCANNING TABLE

PRIOR PROVISIONAL APPLICATION

Applicant claims the benefit of the filing date of Provisional Application Serial No. 60/077,131, filed Mar. 6, 1998.

BACKGROUND OF THE INVENTION

1. Field of the Invention

The present invention relates to surgical tables and, more particularly, to a surgical table having detachable sections which facilitate orthopedic surgery and X-ray scanning.

2. Description of the Prior Art

An increasing number of surgical tables are available for performing various surgical procedures wherein each surgical procedure may require a different configuration for the table. For example, several tables are available having articulated sections wherein the sections may be pivoted relative to each other in order to position a patient in a particular orientation for facilitating surgery. In addition, it is known to provide removable sections for such tables in order to further accommodate the patient positioning requirements of different procedures.

In relation to orthopedic procedures, it is desirable to provide adequate access to the side of a patient's leg, in addition to providing articulated support for positioning the legs of a patient at different angles. Further, there is a recognized ongoing need to provide an orthopedic support capable of providing different configurations to accommodate procedures performed on either the left or right leg of a patient without interfering with a surgeon's access to the leg. Such orthopedic supports typically comprise articulated elongated support struts or spars, extending from an end of a table for supporting the patient. The spars are adapted to mount various accessories for supporting a patient's legs, such as footpiece traction assemblies and leg support plates.

In addition to the procedures which are facilitated by the articulated spars of conventional orthopedic accessories, there is a need to accommodate further procedures without being limited by the adaptability of the surgical table. Specifically, typical orthopedic tables are generally constructed as single purpose tables without provision for additional procedures. In particular, it is desirable to provide a surgical table with the capability to reconfigure the table from an orthopedic configuration to a configuration including an extended patient support surface defined on an X-ray transparent structure. Further, it is desirable to provide such a structure wherein it is possible to X-ray a patient from all angles including oblique angles without interference from non X-ray transparent accessories on the table. While many prior art tables provide X-ray transparent sections, such X-ray transparent sections generally only provide X-ray transparency at certain angles and include portions which will obstruct passage of X-rays at other angles. Further, it is desirable during certain orthopedic procedures to provide a fully transparent table for supporting a patient's legs in order to properly facilitate reorientation of bone sections while monitoring the relative positions of the sections.

In addition to the above described attributes for a surgical table, it is also desirable to provide these attributes in an articulated surgical table adapted for conventional surgical procedures. Such procedures including those which position a patient in various supine positions, as well as positioning a patient in an upright sitting position.

Accordingly, there is a need for a surgical table which is capable of being reconfigured to accommodate different surgical procedures. In particular, there is a need for a surgical table capable of being configured for both orthopedic and X-ray scanning procedures, and which further provides a versatile orthopedic attachment for improved patient support and operator access.

SUMMARY OF THE INVENTION

The present invention provides an articulated surgical table capable of being configured for conventional surgical procedures, and further capable of being alternately configured for orthopedic surgical procedures and configured as a scanning table for unobstructed X-ray scanning.

In the configuration of the surgical table for performing orthopedic operations, an orthopedic attachment is attached to a mounting point located at one end of the surgical table. The orthopedic attachment includes a support frame detachably mounting a pair of spar members for supporting various conventional leg supporting accessories. The spar members may be selectively mounted on or removed from the support frame depending on the requirements of the particular procedure, and the degree of access required by the operator. Further, the support frame preferably provides a plurality of spar mounting points, including a mounting point at the central longitudinal axis of the frame.

The orthopedic attachment further includes a pelvic support plate removably mounted across the top of the support frame. The pelvic support plate is formed with an asymmetrical shape, and preferably includes a cutout forward corner portion. The cutout portion is provided on the affected or broken leg side of the patient to primarily improve X-ray access as well as provide additional surgical access to upper leg areas, while a larger support area is provided on the unaffected or well leg side in order to provide optimal support and leg positioning for the patient. The pelvic support plate may be removed from the support frame and flipped over to position the cutout portion on the opposite side of the table whereby the pelvic support plate may be oriented to provide appropriate support for the patient depending on the particular leg to be operated upon. The pelvic support plate may be provided in various shapes to accommodate differing surgical access and patient support needs.

The orthopedic attachment may be detached from the attachment point on the surgical table and replaced by an elongated scanning table. The scanning table is formed entirely of an X-ray transparent material and is sufficiently long to support a substantial portion of a patient's body, for example, the scanning table is adapted to support at least approximately 48 inches of the length of a patient. The scanning table is further configured to removably support side rails or side mounted accessories wherein the side rails or accessories may be removably clamped to the edges of the table at locations where they will not interfere with X-ray imaging at various orientations or angles including anterior/posterior, posterior/anterior, lateral or oblique, including longitudinal and lateral obliques.

In addition to the above-described functions, the surgical table is also adapted to provide a conventional surgical table support surface for supporting a supine patient. Further, the table may also be configured to support a patient in an upright sitting position, such that the present table provides a variety of conventional patient support orientations in addition to the specialized orthopedic and scanning configurations.

Therefore, it is an object of the present invention to provide an articulated surgical table capable of conventional surgical configuration, and adapted to receive an orthopedic attachment.

It is another object of the invention to provide such a surgical table wherein the orthopedic attachment may be replaced with an X-ray transparent scanning table.

It is a further object of the invention to provide a surgical table including an orthopedic attachment having selectively positionable and removable spar members for supporting the legs of a patient.

It is yet another object of the invention to provide an orthopedic attachment including a pelvic support plate capable of being oriented to support either side of a patient.

Other objects and advantages of the invention will be apparent from the following description, the accompanying drawings and the appended claims.

BRIEF DESCRIPTION OF THE DRAWINGS

FIG. 5 is a perspective view showing the orthopedic attachment mounted to the surgical table with the pelvic support plate removed;

FIG. 7 is a side elevational view of the surgical table with the scanning table attached;

FIG. 8 is a side elevational view of the surgical table configured for supporting a supine patient in conventional surgical procedures.

DETAILED DESCRIPTION OF THE PREFERRED EMBODIMENT

Figure 1:
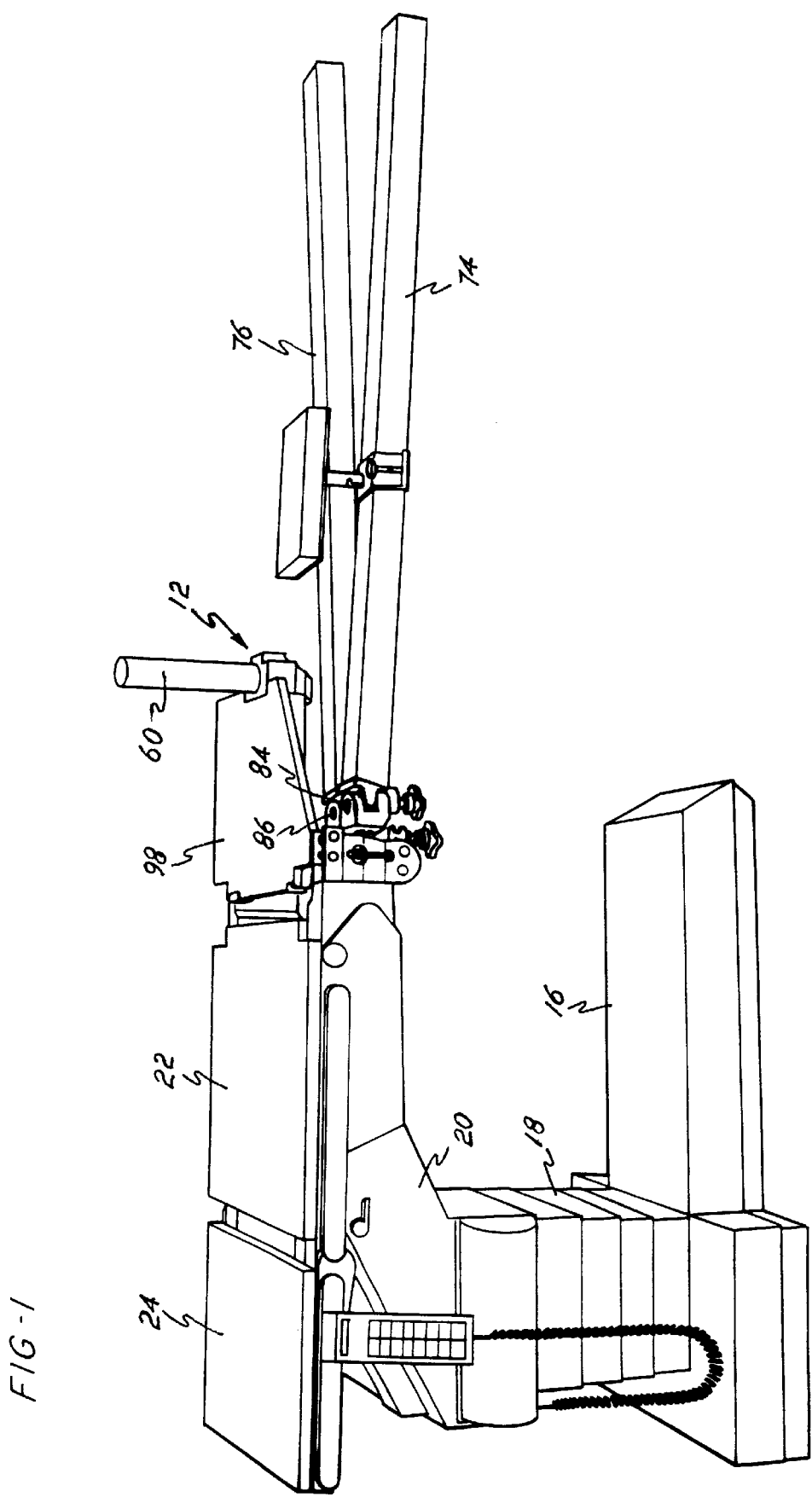
FIG. 1 is a perspective view showing a surgical table supporting the orthopedic attachment of the present invention.
Figure 2:
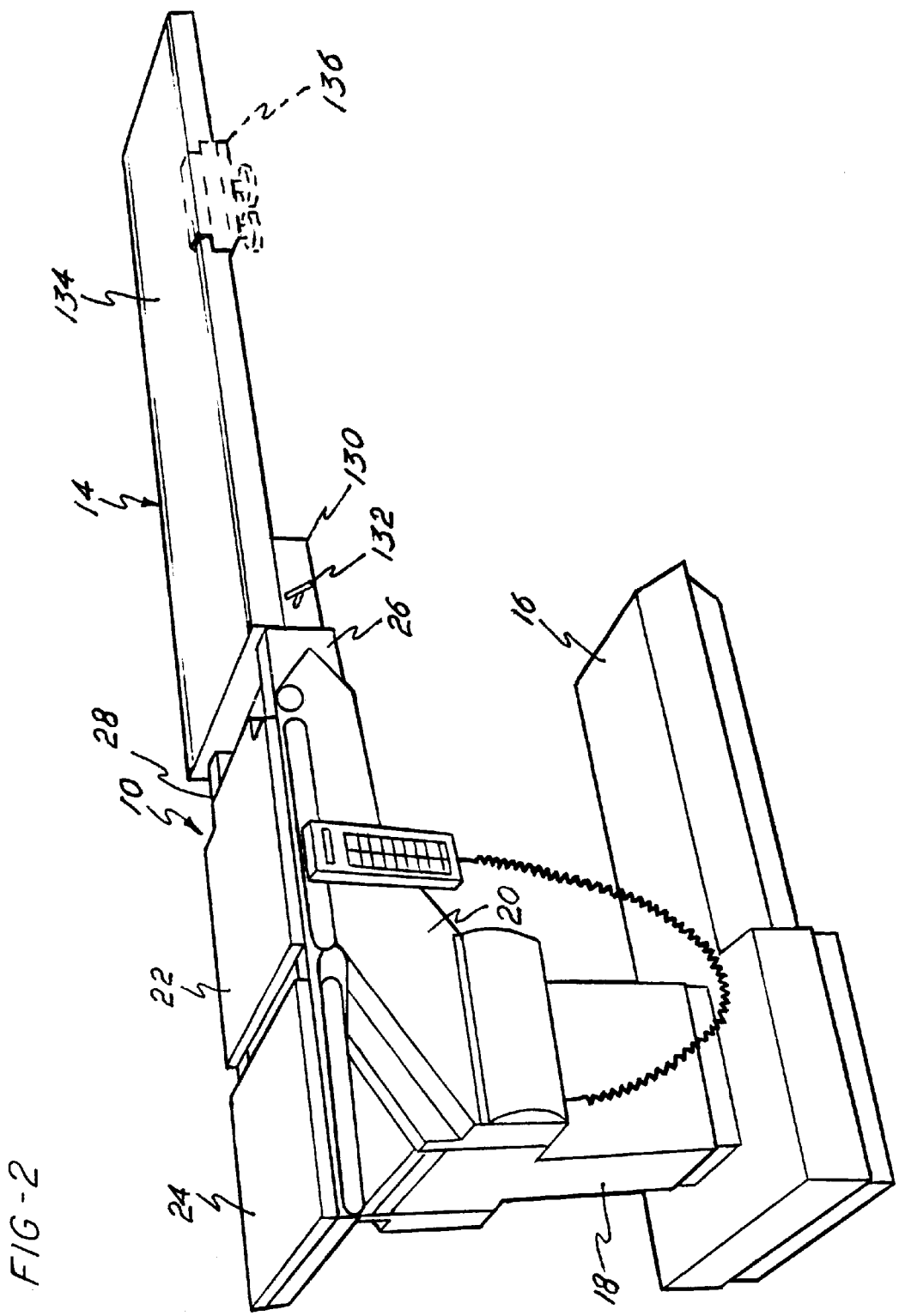
FIG. 2 is a perspective view showing a scanning table supported on the surgical table.

Referring to FIGS. 1 and 2, the surgical table 10 of the present invention is shown alternately configured with an orthopedic attachment 12 and a scanning table attachment 14 for use in orthopedic and scanning procedures.

Figure 3:
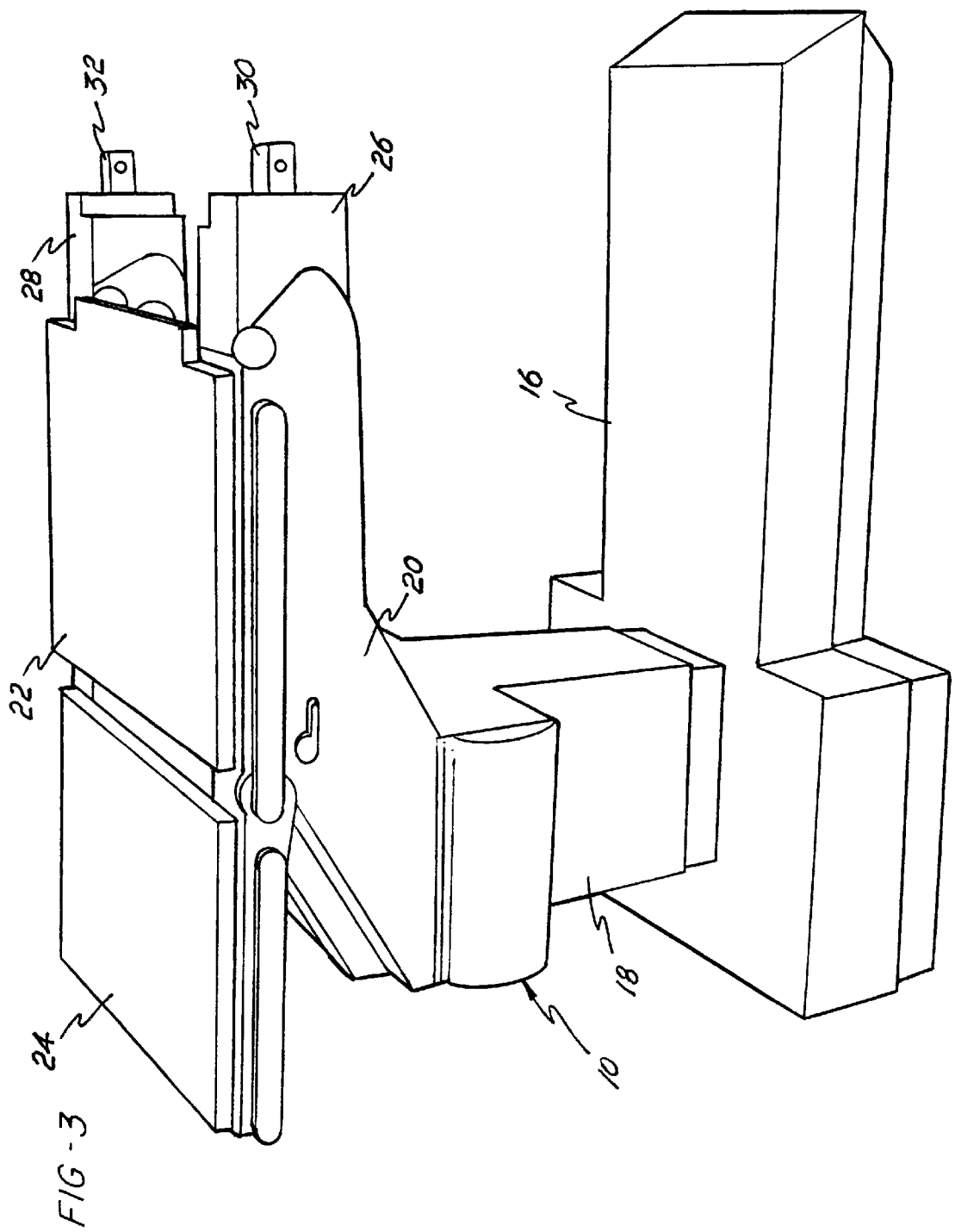
FIG. 3 is a perspective view of the surgical table and showing the attachment points for mounting the attachments of the present invention.

Referring further to FIG. 3, the surgical table 10 includes a base 16 supporting a vertically adjustable column 18, and a support bridge 20 mounted to the top of the support column 18 and rigidly supporting a back section 22 of the table. The support bridge 20 is supported on the top of the column 18 for movement about a lateral tilt axis and a longitudinal tilt axis. In addition, a removable head section 24 is supported at a head end of the back section 22 and is capable of articulated movement relative to the back section 22. At the opposite end of the back section 22, a pair of articulated members 26, 28 are provided including respective mounting studs 30, 32 defining an attachment point for the orthopedic attachment 12 and scanning table attachment 14. It should be noted that the articulated members 26, 28 are driven in pivotal movement by actuators (not shown) located within the bridge 20 whereby the articulated members 26, 28 are particularly adapted to articulate conventional surgical table sections relative to the back section 22. The articulated or pivoting movement of the members 26, 28 may be accomplished in a manner similar to that disclosed for a similar table in U.S. application Ser. No. 08/290,384, assigned to the assignee of the present application, and incorporated herein by reference.

Figure 4:
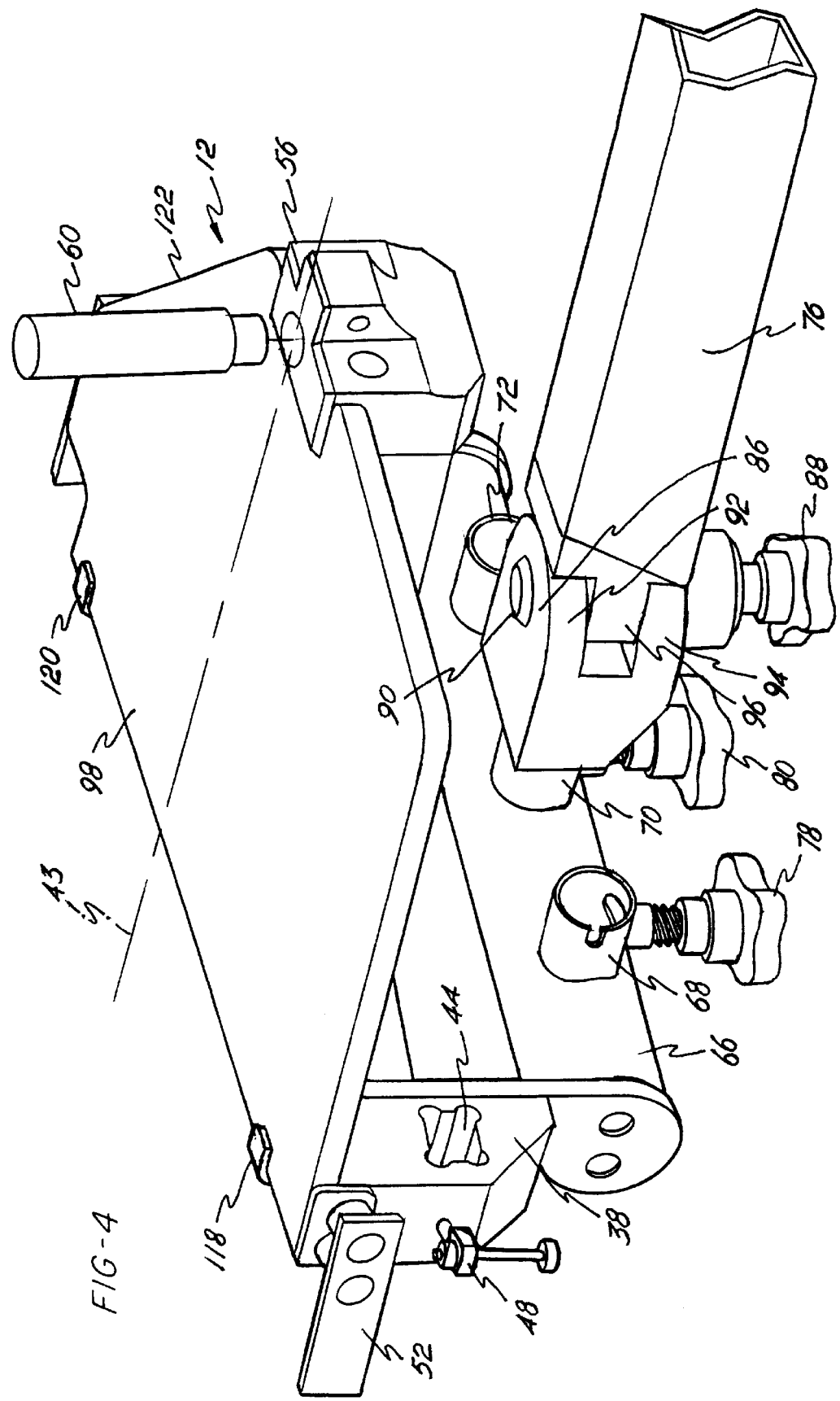
FIG. 4 is a perspective view of the orthopedic attachment of the present invention.

Referring to FIGS. 4 and 5, the orthopedic attachment 12 of the present invention includes a support frame 34 defining an upwardly facing base surface 33 (FIG. 5). The support frame 34 comprises a lateral member 36 rigidly connected to mounting blocks 38, 40 at either end thereof, and rigidly attached to a central longitudinally extending bar 42 which defines a central longitudinal axis 43 for the attachment 12. The mounting blocks 38, 40 each include a respective aperture 44, 46 for receiving the mounting studs 30, 32 therein, and threaded clamping members 48, 50 are provided extending into the respective apertures 44, 46 for contacting the studs 30, 32 in clamping engagement. In addition, short side rail sections 52, 54 are mounted to the outer sides of the mounting blocks 38, 40.

The frame 34 further includes a post mounting block 56 attached to a forward end of the longitudinally extending bar 42. The block 56 includes an aperture 58 for receiving the end of a perineal post 60 whereby the perineal post 60 is supported extending vertically above the frame 34.

A pair of brackets 62, 64 are rigidly attached to and extend downwardly from the mounting blocks 38, 40 and include lower ends rigidly attached to and supporting a cross tube 66. The cross tube 66 includes a plurality of forwardly facing sockets 68, 70, 72 wherein the socket 70 is centrally aligned with the longitudinal axis 43 and the socket 68, 72 are located equally spaced from the socket 70 on either side thereof. The sockets 68, 70, 72 receive the end portions of leg support spars 74, 76 (FIG. 1). It should be noted that, in accordance with the present invention, either both or only one of the leg supporting spars 74, 76 may be used for a given surgical procedure. For example, one spar 74 may be mounted in socket 68, while the other spar 76 is mounted in the central socket 70 wherein the centrally mounted spar 76 is provided with attachments for supporting a leg to be operated on while the other spar 74 is provided for supporting the well leg. Alternatively, a single centrally mounted spar 76 (see FIG. 4) may be provided wherein the spar 76 supports attachments for supporting both the affected leg and the well leg.

Each socket 68, 70, 72 is provided with a respective threaded clamping member 78, 80, 82 which is adapted to thread into engagement with the end of a spar member 74, 76 engaged within the particular socket 68, 70, 72. Further, it should be noted that the spar members 74, 76 are each pivotally mounted at respective pivot points 84, 86 (FIG. 1) adjacent their ends for mounting in the sockets. As illustrated with reference to pivot 86 in FIG. 4, each pivot 84, 86 includes a threaded clamping member 88 threadably engaged with a pin 90 wherein rotation of the clamping member 88 to thread into the pin 90 causes opposing sides 92, 94 of the pivot 86 to clamp down on and prevent pivoting movement of an end 96 of the leg 76. It should be understood that the pivot 84 for the spar 74 is identical to the pivot 86 described above.

Referring to FIGS. 4 and 5, the orthopedic attachment further includes a pelvic support plate 98 which is asymmetrical about the central longitudinal axis 43. The support plate 98 includes a forward edge 100, a rearward edge 102, opposing lateral side edges 104, 106 and opposing upper and lower substantially planar surfaces 108, 110. It should be noted that the planar surfaces 108 and 110 are referred to as "upper" and "lower" for convenience and at the direction that these surfaces will face is interchangeable, as described further below.

The forward edge 100 includes a centrally located slot 112 for engaging around the block 56 and thereby holding the forward edge 100 against lateral movement. In addition, the rearward portions of the lateral side edges 104, 106 are laterally located on the frame 34 by upwardly extending plates 114, 116 mounted to the mounting blocks 38, 40. Also, the rearward edge 102 is located by upwardly and forwardly extending clip members 118, 120 which are supported on the respective mounting blocks 38, 40 and which are adapted to extend forwardly over the rear edge 102 of the pelvic support plate 98. Thus, the pelvic support plate 98 is held against both lateral and longitudinal movement relative to the frame 34, and the rear edge 102 is further held against vertical movement.

The pelvic support plate 98 is provided with a cut out area defined by an angled edge 122 which extends at a non-perpendicular angle from the front edge 100 to one of the lateral side edges 106. The cut out area defined by the edge 122 is provided to accommodate the affected or broken leg while a larger surface is provided on the opposite side to support the well leg and to increase roll stability of the patient's pelvis. Thus, the cut out area defined by edge 122 provides additional access for obtaining X-rays of the affected leg, as well as additional surgical access in certain surgical procedures.

Also, it should be noted that the pelvic support plate 98 may be lifted off of the frame 34 and flipped about the axis 43 such that the side 110 is facing upwardly and the side 108 is facing downwardly. In this manner, the cut out defined by the edge 122 is transferred from the left leg side to the right leg side, and the pelvic support plate 98 may be positioned on the frame 34 in the same manner as previously described. Thus, the pelvic support plate 98 may be quickly adapted to provide the clearance and support needed for a particular patient depending on whether the left or right leg is the affected leg.

Figure 6A:
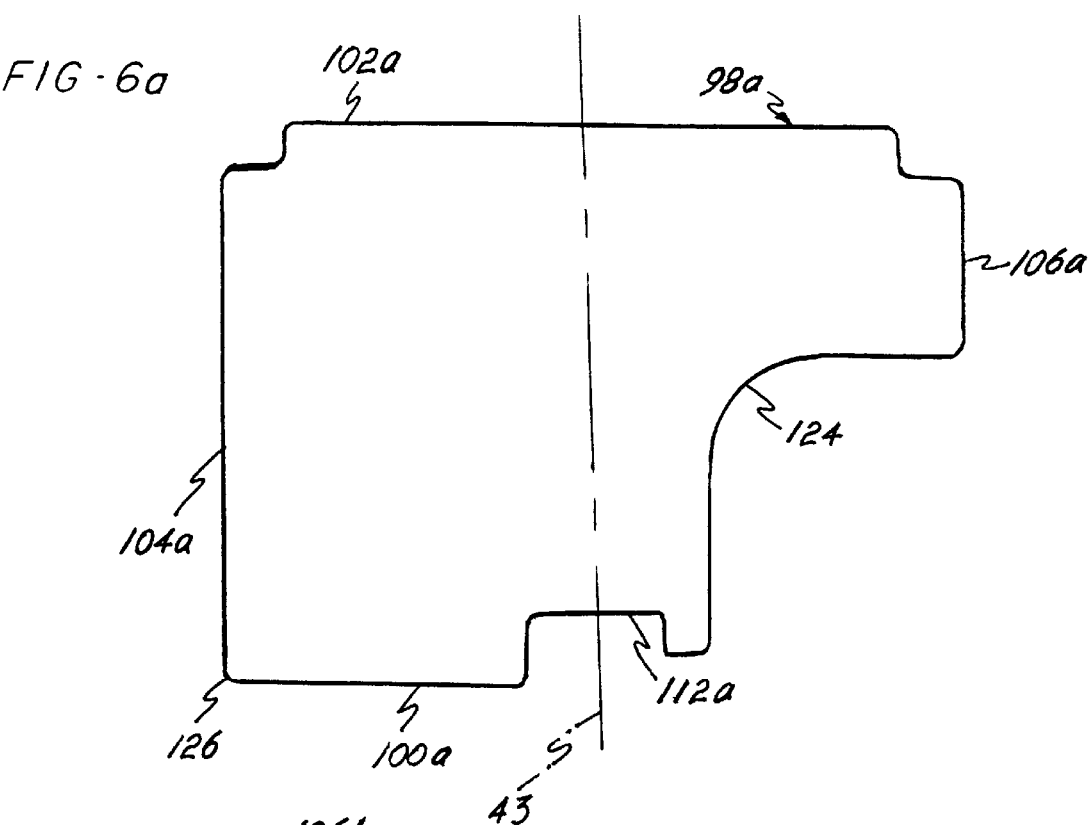
FIG. 6a is a perspective view of a first alternative pelvic support plate shape.

Referring to FIG. 6a, an alternative embodiment of the pelvic support plate is shown and is designated 98a wherein the elements of 98a corresponding to the elements of the support plate 98 previously described are labeled with the same reference numeral having a suffix of the letter a. The cut out area for the pelvic support plate 98a is defined by a large radius concave corner 124 located on one side of the central longitudinal axis 43 and connecting the front edge 100a with the lateral side edge 106a. The opposing lateral side edge 104a and front edge 100a are connected by a convex corner 126, as in the previous embodiment, to provide a larger support surface for the well leg side of the patient, and the area defined by the concave corner 124 may be provided to permit greater operator access, while foregoing the support provided by the angled edge 122 of the support plate 98 of the previous embodiment.

Figure 6B:
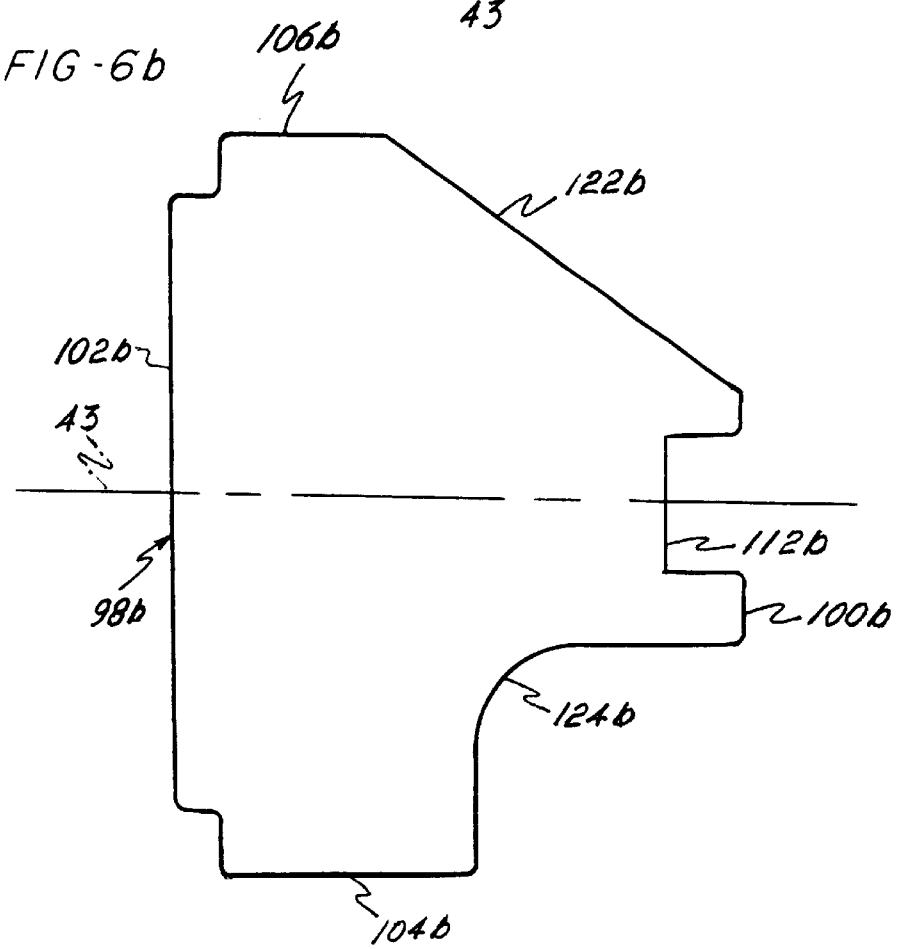
FIG. 6b is a plan view of a second alternative pelvic support plate shape.

Referring to FIG. 6b, a further embodiment of the support plate 98 is shown, and is designated 98b wherein elements corresponding to the elements of the previous two embodiments are labeled with the same reference numeral having a suffix of the letter b. The pelvic support plate 98b combines the cut out areas of the previous two embodiments as defined by a concave corner 124b and an angled edge 122b, and provides a variation for supporting the patient to provide the desired access to either side of the patient, in accordance with the preferences of the operator or surgeon.

It should be noted that a wide variety of pelvic support plates 98 may be provided. Thus, the present invention provides a unique advantage in that an operator may select a particular pelvic support plate configuration in accordance with his or her preferences, and in accordance with the particular needs of any given procedure to be performed on a patient. Further, the ability to quickly lift the support plate 98 from the frame 34 and flip it over to accommodate the particular side of a patient on which the affected leg is located provides further flexibility for the present orthopedic attachment 12.

As noted above, the orthopedic attachment 12 may alternatively be replaced by a scanning table attachment 14 wherein the scanning table attachment 14 is mountable to the table 10 at the same attachment point as the orthopedic attachment 12, as illustrated in FIGS. 2 and 7. The scanning table attachment 14 includes a pair of mounting blocks 130 (only one shown), each including an aperture for receiving a respective mounting stud 30, 32 and having a threaded clamping member 132 (only one shown) for engaging the mounting studs 30, 32 in clamping engagement.

The scanning table attachment 14 includes an elongated X-ray transparent table structure 134 wherein the table structure 134 has a length greater than twice the length of the back section 22, and preferably has an X-ray transparent length of 48 inches or greater whereby the table structure 134 may support a patient from at least the top of the head to the perineum. Significantly, the table section 134 is formed of a high strength, light weight X-ray transparent material, such as carbon fiber, and with the exception of the mounting blocks 130, includes no integral elements which would interfere with transmission of X-rays. Thus, the table structure 134 is adapted to provide a support surface which permits transmission of X-rays from all angles about the table. Further, the table structure is preferably formed with the same construction as that described in U.S. patent application Ser. No. 08/853,629, filed May 9, 1997, assigned to the assignee of the present application, and incorporated herein by reference. In particular, the table structure 134 may be provided with side edges configured to receive detachable clamping members 136 (FIG. 2) which may be detachably clamped to the table structure 134 in areas where they will not interfere with X-ray imaging, or at times when imaging is not being performed and it is necessary to attach accessories 136 to facilitate a surgical procedure.

Figure 9:
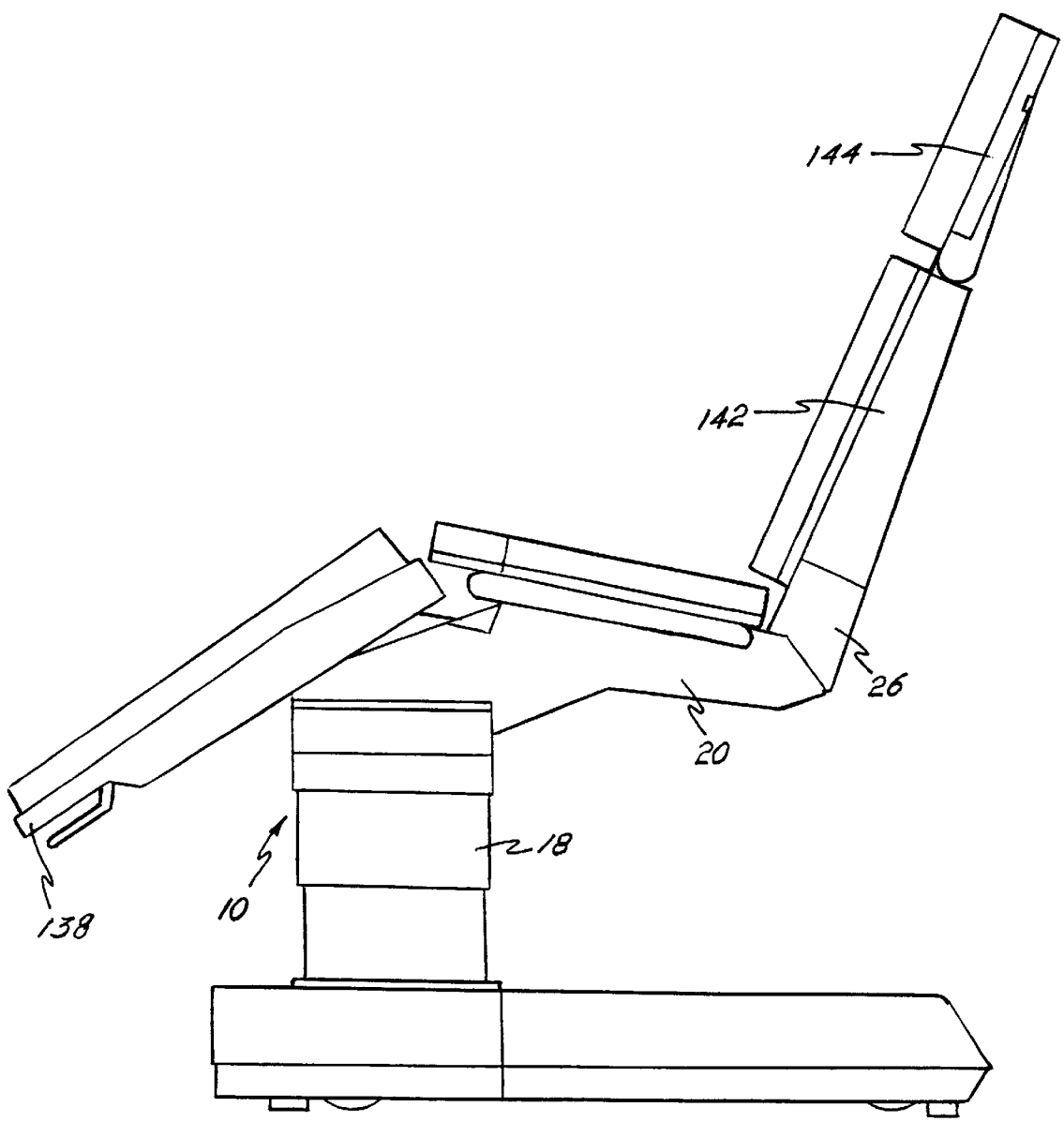
FIG. 9 is a side elevational view of the surgical table configured to support a patient in an upright sitting position.

Referring to FIGS. 8 and 9, conventional configurations for the surgical table 10 are illustrated. In FIG. 8, a perineal section 139 is mounted to the attachment point of the table 10 by means of mounting blocks 140 (only one shown). In addition, a leg section 138 is attached to the perineal section 139. In this configuration of the surgical table, the sections 24, 22, 138 and 139 may be articulated to orient a patient in a wide range of positions for performing a variety of surgical procedures. It should further be noted that the leg section 138 may be removed to facilitate perineal access for ob-gyn, urology or other positions using a lithotomy position.

As seen in FIG. 9, the head section 24, may be replaced with a leg section. such as the leg section 138. In addition, in this configuration, the back section 22 functions as a seat section, and a further back section 142 and head section 144 are supported at the attachment point defined by the articulated members 26, 28.

From the above description, it can be seen that the present surgical table provides a versatile structure including a conveniently located attachment point for alternatively supporting an orthopedic attachment and a scanning table attachment, as well as conventional surgical table attachments. In addition, a unique orthopedic attachment is provided capable of being configured for accommodating surgical procedures on either side of a patient while providing improved access to an operator.

Also, from the above description it should be apparent that the present orthopedic attachment provides a wide range of adjustment to accommodate the preferences of different operators, as well as to accommodate positioning of a patient for different procedures. Specifically, by providing different mounting points for the leg spars, it is possible to laterally position the leg supporting spars to conveniently support the well and affected legs of a patient for any given procedure. Further, by providing a detachable pelvic support plate, it is possible to conveniently orient the plate such that a cut out area may be located on either side of the patient, depending on the need of the particular operation to be performed. It should also be understood that a wide variety of pelvic support plate shapes may be provided in addition to those disclosed herein without departing from the scope of the present invention.

While the form of apparatus herein described constitutes a preferred embodiment of this invention, it is to be understood that the invention is not limited to this precise form of apparatus, and that changes may be made therein without departing from the scope of the invention which is defined in the appended claims.

What is claimed is:

1. An orthopedic surgery apparatus for supporting a patient, said apparatus comprising:

a frame defining an upwardly facing base surface;

a support plate supported on said upwardly facing base surface of said frame and defining a substantially planar upper surface for supporting a patient, said support plate comprising opposing front and rear sides and opposing lateral sides;

said frame comprising upwardly extending portions oriented substantially perpendicular to said upwardly facing base surface, said upwardly extending portions defining a plate retention area and said upwardly extending portions being adjacent said front, rear and lateral sides of said support plate to locate said support plate at a predetermined longitudinal and lateral location on said frame.

2. The apparatus of claim 1 wherein said support plate comprises a centerline intersecting said rear side, and said support plate is asymmetrical with respect to said center line.

3. The apparatus of claim 2 wherein said support plate comprises a cutout area located to one side of said center line and adjacent said front side.

4. The apparatus of claim 3 wherein said front side and a first one of said lateral sides are connected by a concave corner on said one side of said center line to define said cutout area, and said front side and an opposing second one of said lateral sides are connected by a convex corner on an opposing side of said center line.

5. The apparatus of claim 3 wherein said cutout area is defined by an angled edge connecting said front side and one of said lateral sides and extending at a non-perpendicular angle relative to said front side and said one of said lateral sides.

6. The apparatus of claim 2 wherein said support plate comprises opposing planar surfaces, each of said opposing surfaces being locatable against said upwardly facing base surface on said frame to outline reverse locations of said lateral sides with respect to said center line of said support plate.

7. The apparatus of claim 1 comprising upwardly extending clip portions having end portions extending substantially parallel to said base surface wherein said end portions extend over said upper surface of said support plate.

8. The apparatus of claim 1 wherein said frame comprises a plurality of forwardly facing socket portions for removably receiving the end of a leg supporting spar.

9. The apparatus of claim 8 wherein one of said socket portions comprises a central socket located centrally between opposing lateral sides of said frame.

10. The apparatus of claim 9 comprising at least one socket portion on each side of said central socket.

11. The apparatus of claim 1 in combination with a surgical table having mounting studs for mounting table sections on said table, and said frame comprising mounting blocks having apertures for receiving said mounting studs to thereby mount said orthopedic surgery apparatus to said table.

12. The apparatus of claim 1 comprising a perineal post supported on said frame and extending upwardly above said upper surface of said support plate adjacent said front side.

13. An orthopedic surgery apparatus in combination with a surgical table having mounting studs for mounting table sections on the table, said apparatus comprising:

a frame defining an upwardly facing base surface;

a support plate supported on said upwardly facing base surface of said frame and defining a substantially planar upper surface for supporting a patient, said support plate comprising opposing front and rear sides and opposing lateral sides and said support plate being non-symmetrical about a longitudinal center line of said support plate;

said frame comprising upwardly extending portions oriented substantially perpendicular to said upwardly facing base surface, said upwardly extending portions defining a plate retention area and said upwardly extending portions being adjacent said sides of said support plate to locate said support plate at a predetermined longitudinal and lateral location on said frame; and said frame comprising mounting blocks having apertures for receiving the mounting studs of the surgical table to thereby mount the orthopedic surgery apparatus to said table.

14. The apparatus of claim 13 comprising socket portions on said frame and a leg supporting spar engaged with and supported by one of said socket portions.

15. The apparatus of claim 14 wherein one of said socket portions comprises a central socket located centrally between opposing lateral sides of said frame.

16. The apparatus of claim 15 comprising at least one socket portion located on each side of said central socket.

17. The apparatus of claim 13 comprising a perineal post supported on said frame and extending upwardly above said upper surface of said support plate adjacent said front side.

18. The apparatus of claim 13 wherein said surgical table comprising a back section located adjacent said mounting studs, said back section having a length in a longitudinal direction, and comprising an X-ray transparent table structure having a length greater than approximately twice the length of said back section, said X-ray transparent table structure comprising mounting blocks having apertures for mounting said table structure to said surgical table in place of said orthopedic surgery apparatus.

19. An orthopedic surgery apparatus for supporting a patient, said apparatus comprising:
- a frame defining an upwardly facing base surface;
- a support plate supported on said upwardly facing base surface of said frame and defining a substantially planar upper surface for supporting a patient, said support plate comprising opposing front and rear sides and opposing lateral sides; and
- a plurality of sockets defined in said frame for removably receiving and supporting the end of a leg supporting spar.

20. The apparatus of claim 19 wherein each said socket portion comprises a clamping member for engaging and clamping the end of a leg supporting spar engaged with a respective socket portion.

21. The apparatus of claim 19 wherein one of said socket portions comprises a central socket located centrally between opposing lateral sides of said frame.

22. The apparatus of claim 21 comprising at least one socket on each side of said central socket.

23. The apparatus of claim 19 wherein said frame includes upwardly extending portions oriented substantially perpendicular to said upwardly facing base surface, said upwardly extending portions defining a plate retention area and said upwardly extending portions being adjacent said sides of said support plate to locate said support plate at a predetermined longitudinal and lateral location on said frame.

24. The apparatus of claim 19 wherein said support plate is non-symmetrical about a center line intersecting said rear side of said support plate, and said support plate includes opposing planar surfaces and each of said surfaces being locatable against said upwardly facing base surface on said frame to reverse a location of each of said lateral sides with respect to the longitudinal center line of said support plate.

25. The apparatus of claim 19 in combination with a surgical table having mounting studs for mounting said frame, said frame further comprising mounting blocks comprising apertures for receiving said mounting studs whereby said frame is mounted to said surgical table.

26. The apparatus of claim 25 wherein said surgical table comprises a back section located adjacent said mounting studs, said back section having a length in a longitudinal direction, and comprising an X-ray transparent table structure having a length greater than approximately twice the length of said back section, said X-ray transparent table structure comprising mounting blocks having apertures for mounting said table structure to said surgical table in place of said orthopedic surgery apparatus.

* * * * *

UNITED STATES PATENT AND TRADEMARK OFFICE
CERTIFICATE OF CORRECTION

PATENT NO. : 6,295,671 B1  
DATED : October 2, 2001  
INVENTOR(S) : Cyril F. Reesby and James A. Schaefer It is certified that error appears in the above-identified patent and that said Letters Patent is hereby corrected as shown below:

Column 1,  
Line 53, reads "non X-ray" and should read -- nonX-ray --.  
Line 65, reads "Such procedures including those which position…" and should read -- Such procedures include those which position… --.

Column 4,  
Line 35, reads "socket 68, 72" and should read -- sockets 68, 72 --.

Column 5,  
Line 5, reads "for convenience and at the direction" and should read -- for convenience and that the direction --.

Column 6,  
Line 61, reads "… may be replaced with a leg section. Such as …" and should read -- … may be replaced with a leg section, such as … --.

Column 8,  
Line 1, reads "… on said frame to outline reverse locations of …" and should read -- … on said frame to reverse locations of … --.  
Lines 62 and 65, read "comprising" and should read -- including --.

Column 10,  
Line 14, reads "comprising" and should read -- including --.  
Lines 19 and 22, read "comprising" and should read -- including --.

Signed and Sealed this

Twenty-second Day of July, 2003

JAMES E. ROGAN  
*Director of the United States Patent and Trademark Office*

UNITED STATES PATENT AND TRADEMARK OFFICE
CERTIFICATE OF CORRECTION

PATENT NO.    : 6,295,671 B1
DATED         : October 2, 2001
INVENTOR(S)   : Cyril F. Reesby and James A. Schaefer It is certified that error appears in the above-identified patent and that said Letters Patent is hereby corrected as shown below:

Column 7,
Line 35, reads "a support plate supported on said upwardly" and should read
-- a reversible support plate supported by, but not fastened to, said upwardly --.

Column 8,
Line 29, reads "a support plate supported on said upwardly" and should read
-- a reversible support plate supported by, but not fastened to, said upwardly --.

Column 9,
Line 4, reads "a support plate supported on said upwardly" and should read
-- a reversible support plate supported by, but not fastened to, said upwardly --.
Lines 9-11, reads "a plurality of sockets defined in said frame for removably receiving and supporting the end of a leg supporting spar" and should read -- a centerline intersecting said rear side, said support plate being asymmetrical with respect to said center line; and a cutout area located to one side of said center line and adjacent said from side --.

Signed and Sealed this

Seventh Day of October, 2003

JAMES E. ROGAN
*Director of the United States Patent and Trademark Office*